United States Patent
Renne et al.

(10) Patent No.: US 9,034,354 B2
(45) Date of Patent: May 19, 2015

(54) BACTERIOSTATIC AND ANTI-COLLAGENOLYTIC DENTAL MATERIALS THROUGH THE INCORPORATION OF POLYACRYLIC ACID MODIFIED CUI NANOPARTICLES

(71) Applicants: MUSC Foundation for Research Development, Charleston, SC (US); Clemson University, Clemson, SC (US)

(72) Inventors: Walter George Renne, Charleston, SC (US); Anthony Samuel Mennito, Charleston, SC (US); Michael Gerard Schmidt, Charleston, SC (US); Jompobe Vuthiganon, Charleston, SC (US); George Chumanov, Clemson, SC (US)

(73) Assignees: MUSC Foundation for Research Development, Charleston, SC (US); Clemson University, Clemson, SC (US)

( * ) Notice: Subject to any disclaimer, the term of this patent is extended or adjusted under 35 U.S.C. 154(b) by 0 days.

(21) Appl. No.: 13/900,942

(22) Filed: May 23, 2013

(65) Prior Publication Data
US 2014/0037705 A1    Feb. 6, 2014

Related U.S. Application Data

(60) Provisional application No. 61/650,877, filed on May 23, 2012.

(51) Int. Cl.

| A61K 33/34 | (2006.01) |
|---|---|
| C01G 3/04 | (2006.01) |
| A61K 6/00 | (2006.01) |
| C01G 3/02 | (2006.01) |
| C01G 3/12 | (2006.01) |
| A61K 6/083 | (2006.01) |
| A61C 5/08 | (2006.01) |

(52) U.S. Cl.
CPC .......... *A61K 33/34* (2013.01); *A61K 6/007* (2013.01); *Y10S 977/773* (2013.01); *A61K 6/0835* (2013.01); *C01G 3/04* (2013.01); *C01G 3/02* (2013.01); *C01G 3/12* (2013.01); *A61C 5/08* (2013.01)

(58) Field of Classification Search
CPC ......... A61K 6/00; A61K 6/0255; A61K 6/04; A61K 6/002; A61K 6/0032; A61K 6/02; A61K 6/007; C01G 3/00; C01G 3/02
See application file for complete search history.

(56) References Cited

U.S. PATENT DOCUMENTS

| 5,063,257 A * | 11/1991 | Akahane et al. ............. 523/116 |
| 5,374,664 A | 12/1994 | Zalsman et al. |
| 5,456,602 A | 10/1995 | Sakuma |
| 5,733,949 A | 3/1998 | Imazato et al. |
| 6,124,374 A | 9/2000 | Kolias et al. |
| 6,355,704 B1 | 3/2002 | Nakatsuka et al. |
| 2004/0002557 A1 * | 1/2004 | Qian ............................ 523/113 |
| 2012/0301528 A1 * | 11/2012 | Uhlmann et al. ............. 424/405 |
| 2012/0301530 A1 * | 11/2012 | Uhlmann et al. ............. 424/405 |
| 2012/0301531 A1 * | 11/2012 | Uhlmann et al. ............. 424/405 |
| 2012/0301533 A1 * | 11/2012 | Uhlmann et al. ............. 424/419 |
| 2013/0171225 A1 * | 7/2013 | Uhlmann et al. ............. 424/405 |
| 2013/0171266 A1 * | 7/2013 | Uhlmann et al. ............. 424/632 |
| 2013/0315972 A1 * | 11/2013 | Krasnow et al. ............. 424/409 |

OTHER PUBLICATIONS

Z Ahmad, MA Vargas-Reus, R Bakhshi, F Ryan, GG Ren, F Oktar, RP Allaker. "Antimicrobial Properties of Electrically Formed Elastomeric Polyurethane-Copper Oxide Nanocomposites for Medical and Dental Applications." Methods in Enzymology, vol. 509, 2012, pp. 87-99, available online May 5, 2012.*

G Ren, D Hu, EWC Cheng, MA Vargas-Reus, P Reip, RP Allaker. "Characterisation of copper oxide nanoparticles for antimicrobial applications." International Journal of Antimicrobial Agents, vol. 33, 2009, pp. 587-590.*

A Pramanik, D Laha, D Bhattacharya, P Pramanik, P Karmakar. "A novel study of antibacterial activity of copper iodide nanoparticle mediated by DNA and membrane damage." Colloids and Surfces B: Biointerfaces, vol. 96, 2012, pp. 50-55.*

Ahmad et al., "Antimicrobial properties of electrically formed elastomeric polyurethane-copper oxide nanocomposites for medical and dental applications," *Methods Enzymol.*, 509:87-99, 2012. Available online May 5, 2012.

Allaker RP, "The use of nanoparticles to control oral biofilm formation," *J Dent Res.*, 89(11):1175-86, 2010.

Boldyryeva et al., "High-fluence implantation of negative metal ions into polymers for surface modification and nanoparticle formation," *Surf Coat Tech.*, 196:373-377, 2005.

Morones et al., "The bactericidal effect of silver nanoparticles," *Nanotechnology*, 16:2346-2353, 2005.

Shaini et al., "A comparison of the mechanical properties of a gallium-based alloy with a spherical high-copper amalgam," *Dent Mater.*, 17(2):142-8.28, 2001.

Sill et al., "Electrospinning: Applications in drug delivery and tissue engineering," *Biomaterials*, 29(13):1989-2006, 2008.

\* cited by examiner

*Primary Examiner* — Frederick Krass
*Assistant Examiner* — Isaac Shomer
(74) *Attorney, Agent, or Firm* — Parker Highlander PLLC

(57) ABSTRACT

Provided are antibacterial and antimicrobial surface coatings and dental materials by utilizing the antimicrobial properties of copper chalcogenide and/or copper halide (CuQ, where Q=chalcogens including oxygen, or halogens, or nothing). An antimicrobial barrier is created by incorporation of CuQ nanoparticles of an appropriate size and at a concentration necessary and sufficient to create a unique bioelectrical environment. The unique bioelectrical environment results in biocidal effectiveness through a multi-factorial mechanism comprising a combination of the intrinsic quantum flux of copper ($Cu^0$, $Cu^{1+}$, $Cu^{2+}$) ions and the high surface-to-volume electron sink facilitated by the nanoparticle. The result is the constant quantum flux of copper which manifests and establishes the antimicrobial environment preventing or inhibiting the growth of bacteria. The presence of CuQ results in inhibiting or delaying bacterial destruction and endogenous enzymatic breakdown of the zone of resin inter-diffusion, the integrity of which is essential for dental restoration longevity.

18 Claims, 4 Drawing Sheets

BACTERIOSTATIC AND ANTI-COLLAGENOLYTIC DENTAL MATERIALS THROUGH THE INCORPORATION OF POLYACRYLIC ACID MODIFIED CUI NANOPARTICLES

This application claims priority to U.S. Provisional Application No. 61/650,877, filed May 23, 2012, the entire contents of which are herein incorporated by reference.

This invention was made with Government support under Grant No. P20RR017696 awarded by the National Institute of Health, SC COBRE for Oral Health Research and Grant No. DE-FG02-06ER46342 awarded by the Department of Energy. The Government has certain rights in the invention.

BACKGROUND OF THE INVENTION

1. Field of the Invention

The invention is directed to a bacteriostatic/cidal and anti-collagenolytic adhesive used to control the invasion and proliferation of microorganisms. In some embodiments, the invention is directed to an antimicrobial dental adhesive/restorative material used to control microbial pathogens within the oral cavity.

2. Background of the Invention

An attempt to manage two of the most common human maladies in the world, tooth decay and periodontal disease, must be waged in an environment that is continually bathed in saliva that is filled with thousands of bacterial species present as a complex population numbering in the hundreds of millions of bacteria per milliliter of salvia. In addition, this environment also includes a multitude of enzymes, minerals, yeasts, foodstuffs and more. Dentistry has made many advances in restorative materials and technology to manage these diseases. These advancements in adhesive dentistry and esthetic filling materials are certainly notable and significant. However, restoration durability remains a major problem.

It is estimated that over 70% of new dental restorations are a consequence of old dental restorations that have failed. In 2005, 166 million dental restorations were placed in the United States and it can be estimated that over 83 million of those were replacements of failed dental restorations. The most popular restorative material is resin based composite (RBC). RBC restorative materials are popular due to their excellent wear, lifelike esthetics and ability to conserve tooth structure.

Currently, 65% of restorations in the United States are made of RBC. RBC popularity is rising due to several factors but primarily by patient demand for esthetic restorations. Despite their popularity, RBC restorations have limited clinical longevity. It is estimated that the cost of replacement of failing composite restorations is 5 billion dollars annually. Bacterial infiltration is the most frequent complication of RBC restorations resulting in recurrent caries as the principle cause of failure.

In recognition of these shortcomings, Imazato and colleagues conducted a series of experiments where composite resins containing an antibacterial monomer, 12-methacryloyloxydodecylpyridinium bromide (MDPB) were evaluated for its ability to withstand the degradative and destructive activities manifested by cariogenic microbes present in the oral cavity. The bactericidal activity of the adhesive resin containing MDPB was evaluated by subjecting discs constructed of composite resin with and without MDPB in the presence of a cariogenic microbe, *Streptococcus mutans*. These studies were remarkable in that they found that the numbers of bacteria recovered from the discs containing MDPB were reduced by 97%. Imazato and colleagues also evaluated the tensile bond strength of the composite resin containing MDPB by utilizing extracted human molars that were free of restorations and carious lesions. They found that the tensile bond strength of the MDPB resin was not significantly different from that of the control. A resin based on this technology is disclosed in U.S. Pat. Nos. 5,733,949 and 6,355,704 and marketed under the name Clearfil™ SE Protect bond by Kuraray Dental (www.kuraray-am.com/).

However, while the technology disclosed in U.S. Pat. Nos. 5,733,949 and 6,355,704 attempts to minimize bacterial retention and invasion of dental bonding agents, certain deficiencies continue to exist. Little evidence exists on the longevity of MDPB's antimicrobial activity and it has been suggested that it is short lived possibly due to decreased antimicrobial activity after light curing. Indeed, much of the independent research that shows MDPB has antimicrobial activity against oral microorganism did not use polymerized MDPB and thus does not correlate accurately to the clinical situation which necessitates polymerization of the MDPB adhesive resin.

Likewise, glass ionomer (GI) has always been touted for its bacteriostatic effect due to high concentrations of fluoride release. However, some research data indicates that while they do limit bacterial proliferation, it is not entirely antimicrobial. This is especially true because GI's antimicrobial properties are a function of the release of fluoride which is a component of the GI matrix. Thus, as the restoration ages, fluoride release decreases. In addition, poor antimicrobial resistance coupled with glass ionomer's recognized deficiencies including poor resistance to surface wear and poor resistance to fracturing means that bacterial invasion of the restoration is an ongoing process undermining the longevity of the restoration itself.

Therefore, a more efficacious and longer-lasting bacteriostatic and/or bacteriocidal agent for use in biological implants, especially dental ones, are needed.

SUMMARY OF THE INVENTION

The present invention provides antibacterial and antimicrobial surface coatings and dental materials by utilizing the antimicrobial properties of copper chalcogenide and/or copper halide (CuQ, where Q=chalcogens including oxygen, or halogens, or nothing). An antimicrobial barrier is created by incorporation of CuQ nanoparticles of an appropriate size and at a concentration necessary and sufficient to create a unique bioelectrical environment. This unique bioelectrical environment results in biocidal effectiveness through a multi-factorial mechanism comprising a combination of the intrinsic quantum flux of copper ($Cu^0$, $Cu^{1+}$, $Cu^{2+}$) ions and the high surface-to-volume electron sink facilitated by the nanoparticle. The result is the constant quantum flux of copper which manifests and establishes the antimicrobial environment preventing or inhibiting the growth of bacteria. The presence of CuQ results in inhibiting or delaying bacterial destruction and endogenous enzymatic breakdown of the zone of resin inter-diffusion, the integrity of which is essential for dental restoration longevity.

Therefore, in one exemplary embodiment, the invention provides an antibacterial dental resin comprising a dental resin and an antimicrobial amount of CuQ nanoparticles diffused therein. In some embodiments, the CuQ nanoparticles are coated with polymers containing carboxylic groups (PCCG) such as polyacrylic acid (PAA). In some exemplary embodiments, the CuQ nanoparticles are 20 nm or less.

In another exemplary embodiment, the invention comprises an antimicrobial dental sealant comprising a dental sealant; and an antimicrobial dental resin including an antimicrobial amount of CuQ nanoparticles diffused therein. In various embodiments the CuQ nanoparticles are coated with PCCG. In some exemplary embodiments, the CuQ nanoparticles are 20 nm or less.

In yet another exemplary embodiment, the invention comprises composition useful in preventing or inhibiting the growth of biofilms on a surface the composition comprising an adhesive, composite resin or adhesive resin containing an antimicrobial amount of CuQ nanoparticles diffused therein. In some exemplary embodiments the composition includes contained in a paint or dye. In various embodiments the CuQ nanoparticles are coated with PCCG. In some exemplary embodiments, the CuQ nanoparticles are 20 nm or less.

In still another exemplary embodiment, the invention provides an indwelling antibacterial device including an implantable surface coated with an adhesive containing an antimicrobial amount of CuQ nanoparticles diffused therein. In various embodiments, the surface is a suture, a staple, a stent, a plate, a screw, a pin or the like that is biocompatible and can be temporarily or permanently fixed internally in a patient. In some exemplary embodiments, the surface is the surface of the CuQ nanoparticles that are implanted, either uncontained or contained in a freely diffusible container within the body at the site of an infection. In various embodiments the CuQ nanoparticles are coated with PCCG. In these exemplary embodiments, the CuQ nanoparticles are 200 nm or less.

In yet another exemplary embodiment, the invention provides an antibacterial dental restorative composition including a glass ionomer and an antimicrobial amount of CuQ nanoparticles diffused therein. In various embodiments the CuQ nanoparticles are coated with PCCG. In some exemplary embodiments, the CuQ nanoparticles are 20 nm or less.

In another exemplary embodiment, the invention provides an antimicrobial cement for use in dental restorations including a glass ionomer and an antimicrobial amount of CuQ nanoparticles diffused in the glass ionomer. In various embodiments the CuQ nanoparticles are coated with PCCG. In some exemplary embodiments, the CuQ nanoparticles are 20 nm or less.

In still another exemplary embodiment, the invention provides a method of preventing tooth decay including applying a CuQ nanoparticle containing dental resin to a tooth surface. In some exemplary embodiments, the CuQ nanoparticle containing resin is applied above the gum line. In other exemplary embodiments, the CuQ nanoparticle containing resin is applied below the gum line. In various embodiments the CuQ nanoparticles are coated with PCCG. In some exemplary embodiments, the CuQ nanoparticles are 20 nm or less.

In another exemplary embodiment, the invention provides a method to prevent or inhibit periodontal disease comprising applying a CuQ nanoparticle containing dental resin within a periodontal pocket. In some exemplary embodiments, the CuQ nanoparticle containing resin is applied above the gum line. In other exemplary embodiments, the CuQ nanoparticle containing resin is applied below the gum line. In various embodiments the CuQ nanoparticles are coated with PCCG. In various exemplary embodiments, the CuQ nanoparticles are 20 nm or less.

In another exemplary embodiment, the invention provides a method of preventing or inhibiting dental caries comprising applying an antimicrobial dental sealant to a tooth the antimicrobial sealant including an antimicrobial dental resin including an antimicrobial amount of CuQ nanoparticles diffused therein. In some embodiments according to the invention the tooth is a child's tooth. In various embodiments the CuQ nanoparticles are coated with PCCG. In various exemplary embodiments, the CuQ nanoparticles are 20 nm or less.

In another exemplary embodiment, the invention provides a method for increasing the successful establishment of dental implants comprising applying an antimicrobial dental resin to a critical area including the adjacent tooth surfaces and those immediately below the gum line of the teeth surrounding the implant, the antimicrobial dental resin including an antimicrobial amount of CuQ nanoparticles diffused therein. In various embodiments the CuQ nanoparticles are coated with PCCG. In various exemplary embodiments, the CuQ nanoparticles are 20 nm or less. In some embodiments the antimicrobial dental resin is applied to the critical area prior to implantation. In various embodiments, the antimicrobial dental resin is applied to the critical area one or more times after implantation of the implant. In various embodiments the implant is an osseointegrative implant.

In another exemplary embodiment, the invention provides a method for inhibiting the localized invasion and proliferation of microorganisms in a critical area of a dental implant comprising applying an antimicrobial dental resin to the critical area of the site of the implant wherein the antimicrobial dental resin includes an antimicrobial amount of CuQ nanoparticles diffused therein. In some exemplary embodiments, the critical area is the adjacent tooth surfaces and those immediately under the crown and associated implant gum line of implant as well as those of the surrounding teeth. In various embodiments the CuQ nanoparticles are coated with PCCG. In various exemplary embodiments, the CuQ nanoparticles are 20 nm or less. In some embodiments the antimicrobial dental resin is applied to the critical area prior to implantation. In various embodiments, the antimicrobial dental resin is applied to the critical area one or more times after implantation of the implant. In various embodiments the implant is an osseointegrative implant.

In another embodiment, the invention provides a method of reducing the incidence of dental carries resulting from the placement of orthodontic appliances in a patient comprising applying an antimicrobial dental resin to the surface of a tooth at the site of attachment of orthodontic bands, wherein the antimicrobial dental resin includes an antimicrobial amount of CuQ nanoparticles diffused therein. In various embodiments the CuQ nanoparticles are coated with PCCG. In various exemplary embodiments, the CuQ nanoparticles are 20 nm or less. In some embodiments, antimicrobial dental resin is applied prior to placement of the orthodontic appliance. In various embodiments, the antimicrobial dental resin is applied to the tooth one or more times after placement of the orthodontic appliance.

In yet another exemplary embodiment, the invention provides a method for increasing the success of endodontic procedures comprising treating the site of the endodontic procedure with an antimicrobial dental resin prior to packing the site with packing materials, wherein the antimicrobial dental resin includes an antimicrobial amount of CuQ nanoparticles diffused therein. In various embodiments the CuQ nanoparticles are coated with PCCG. In various exemplary embodiments, the CuQ nanoparticles are 20 nm or less.

In another exemplary embodiment, the invention provides a method of inhibiting or limiting the infection resulting from the insertion of an indwelling invasive appliance in a patient comprising coating the surface of the indwelling invasive appliance with an antimicrobial adhesive, composite resin or adhesive resin prior to inserting the indwelling appliance in the patient, wherein the antimicrobial composite resin includes an antimicrobial amount of CuQ nanoparticles diffused therein. In some embodiments, the indwelling device is a short-term device while in other embodiments the indwelling device is a long-term device. In various embodiments, the indwelling device is any implantable device such as, a urinary catheter, a portacath, a stent, a pacemaker, a heart valve, bypass grafts, artificial joints, and central nervous system shunts. In various embodiments the CuQ nanoparticles are coated with PCCG. In various exemplary embodiments, the CuQ nanoparticles are 20 nm or less.

In other exemplary embodiments, the invention provides a method of inhibiting or reducing the establishment of biofilms on a surface comprising coating the surface with an antimicrobial adhesive, composite resin or adhesive resin wherein the antimicrobial composite resin includes an antimicrobial amount of CuQ nanoparticles diffused therein. In various embodiments the CuQ nanoparticles are coated with PCCG. In various exemplary embodiments, the CuQ nanoparticles are 200 nm or less.

In still other exemplary embodiments, the invention provides a method of treating an internal infection comprising: implanting a surface treated with an adhesive, composite resin or adhesive resin containing an antimicrobial amount of CuQ nanoparticles diffused therein. In some embodiments, the surface includes, but is not limited to, the surface of a suture, a stent, a staple, a plate, a screw, a pin, a catheter, a bridge, a prophylactic device or the like. In various embodiments, the surface is the surface of the CuQ nanoparticles either uncontained or contained within a freely diffusible container. In various embodiments the CuQ nanoparticles are coated with PCCG. In various exemplary embodiments, the CuQ nanoparticles are 20 nm or less.

In another exemplary embodiment, the invention provides a method of inhibiting or preventing the development of dental caries in a patient, the method comprising treating the surface of a tooth with a restorative material including a glass ionomer containing an antimicrobial amount of CuQ nanoparticles diffused therein. In various embodiments the CuQ nanoparticles are coated with PCCG. In various exemplary embodiments, the CuQ nanoparticles are 20 nm or less.

In another exemplary embodiment, the invention provides a method for increasing the bonding and life span of dental restorations comprising placing a liner material under a composite resin restoration, the liner material comprising a glass ionomer containing an antimicrobial amount of CuQ nanoparticles diffused therein. In some exemplary embodiments, the CuQ nanoparticles are coated with PCCG. In various exemplary embodiments, the CuQ nanoparticles are 20 nm or less.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be apparent from the description, as set forth hereinafter.

BRIEF DESCRIPTION OF THE FIGURES

Various exemplary embodiments of the compositions and methods according to the invention will be described in detail, with reference to the following figures wherein.

DETAILED DESCRIPTION OF THE EXEMPLARY EMBODIMENTS

Figure 1:
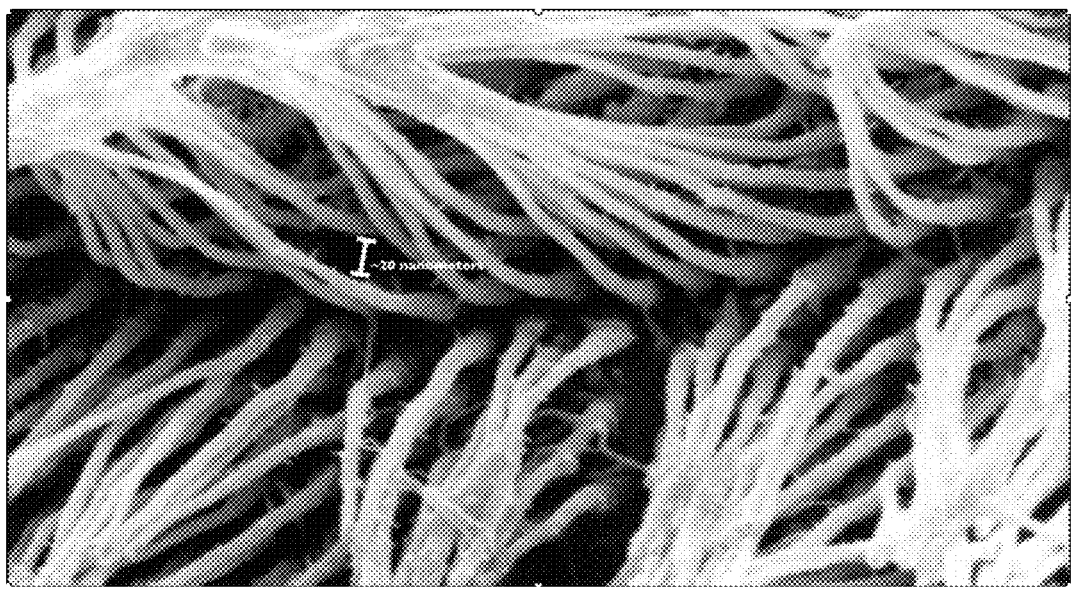
FIG. 1 is an electron micrograph of a collagen bundle in the demineralized dentin of a tooth. Bar=20 nm.

Provided are antibacterial and antimicrobial surface coatings and dental materials by utilizing the antimicrobial properties of copper chalcogenide and/or copper halide (CuQ, where Q=chalcogens including oxygen, or halogens, or nothing). An antimicrobial barrier is created by incorporation of CuQ nanoparticles of an appropriate size and at a concentration necessary and sufficient to create a unique bioelectrical environment. The unique bioelectrical environment results in biocidal effectiveness through a multi-factorial mechanism comprising a combination of the intrinsic quantum flux of copper ($Cu^0$, $Cu^{1+}$, $Cu^{2+}$) ions and the high surface-to-volume electron sink facilitated by the nanoparticle. The result is the constant quantum flux of copper which manifests and establishes the antimicrobial environment preventing or inhibiting the growth of bacteria. The presence of CuQ results in inhibiting or delaying bacterial destruction and endogenous enzymatic breakdown of the zone of resin inter-diffusion, the integrity of which is essential for dental restoration longevity.

It is thought that the intrinsic antimicrobial property of Cu, $Cu^{1+}$, and $Cu^{2+}$ requires a sufficient quantum effect that will confer an antimicrobial property while limiting the toxicity that might manifest to host cells. Here it is the quantum effect on the nano-scale that manifests in CuQ being able to form and serve as a sufficient antimicrobial barrier. This novel realization proceeds from the inventors appreciation of the teachings of Paul Drude who argued that the transport properties of metals might be accounted for by assuming that their electrons were free and within a state of thermal equilibrium with respect to their atoms. (See, Lehrbuch der Optik, by Drude, Paul 1900, translated into English as, "The Theory of Optics" 1902.) Drude's insights coupled with advances added by H. A. Lorentz who added quantitation to the theory assuming that the mean free path of electrons was limited by collisions amongst the atoms which resulted in the derivation of Ohm's law for electrical conductivity. Lorentz's treatment of metals was revised by A. J. W. Sommerfeld using quantum statistics to control for its limitations, removing the difficulty of resolving conflicts with specific heat without losing the successful description of transport properties. Sommerfeld applied Fermi-Dirac statistics to the Drude model of electrons in metals. The new theory solved many of the problems predicting thermal properties the original model had and became known as the Drude-Sommerfeld model. The theory of Sommerfeld remains the basis for understanding the majority of properties associated with transport in metals and semi-conductors.

Without being held to any particular theory, it is believed that the metallic nature of CuQ is responsible in forming a partial positive, electron-withdrawing complex. In the case of CuQ, a nano-galvanic reaction will manifest between the bacterial population and the nano-metallic particles within the adhesive. Such an interaction between the microbial community (bacteria, fungi and viruses) manifests itself as the antimicrobial property made useful by the instant invention.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

As used herein, "dental sealant" means a dental treatment consisting of applying a plastic material to one or more teeth, for the intended purpose of preventing dental caries (cavities) or other forms of tooth decay. As used herein, the term "endodontic procedure" refers to any procedure which exposes the tooth pulp and the tissues surrounding the root of a tooth. As used herein, the term "resin sealer" means a resin material used often in conjunction with gutta percha (or other packing material) as a sealing material to fill in voids and prevent bacterial invasion of the canal space after root canal treatment. As used herein the term "coupled to iodide" means forming a binary metal halide inorganic polymer with copper. As used herein, the term "orthodontic bands" means metal rings used in orthodontics to anchor an appliance to the teeth or secure an archwire to the molars or premolars. Orthodontic bands are temporally cemented to teeth with cement designed specifically for the use with bands. As used herein, the term "dental cement" means any of various bonding substances that are placed in the mouth as a viscous liquid and set to a hard mass; used in restorative and orthodontic dental procedures as luting (cementing) agents, as protective, insulating, or sedative bases, and as restorative materials. Examples of dental cements include phosphate (zinc phosphate, silico phosphate) cements, polycarboxylate (zinc polycarboxylate) (glass ionomer) cements, phenolate (zinc oxide-eugenol and ethoxybenzoic acid (EBA)) cements and resin (polymeric) cements.

As used herein, the term "treating" when used in conjunction with a physical object means "applying" or "coating". A dental adhesive is a special resin engineered to penetrate the tooth surface and bond the filling material to the tooth. It is placed in a thin coat, in a separate step prior to placing the filling material. The filling material is called composite resin is the actual restoration. One is the glue and the other is the filling. Both contain resin, both can be modified with the antimicrobial nanoparticles. As used herein CuQ means copper chalcogenide and/or copper halide or other trace impurities (CuQ, where Q=chalcogens including oxygen, or halogens, other impurities or nothing). Thus, CuQ can range from pure copper to a copper having various impurities. As used herein, the acronym "PCCG" means "polymers containing carboxylic groups" such as, but not limited, to polyacrylic acid (PAA), carboxymethyl cellulose, maleic acid copolymers (for example, acrylic acid maleic acid copolymer, styrene maleic acid copolymer) carboxylated polybutadienes, polyalginates, polyamino carboxylic acids.

As used herein, the term "freely diffusible container" means a biocompatible container that has pores or openings allowing for the containment of nanoparticles but allowing for the diffusion of ionic CuQ ($Cu^{2+}$). Freely diffusible containers may be made of biocompatible mesh or fabric such as Gore-Tex® (pore size 0.2 nm) or specialty nano-woven fabrics made by electrospinning See for example, Electrospinning: Applications in drug delivery and tissue engineering, Travis J. Sill, Horst A. von Recum, Biomaterials, Volume 29, Issue 13, May 2008, Pages 1989-2006, the contents of which are incorporated herein in their entirety for all purposes. As used herein, the term "prophylactic device" means a device that has a surface that can be treated with the antimicrobial resin or adhesive disclosed herein and which can be implanted in an animal (including human) to prevent or treat a microbial infection.

As used herein, the term "biofilm" means an aggregate of microorganisms in which cells adhere to each other on a surface. As used herein, the term "medical surface" means the surface of a medical device whether used by a doctor or health care professional externally or internally on a patient. As used herein the term "industrial surface" refers to all surfaces that are not medical surfaces. Industrial surfaces include those surfaces in a domestic setting or a factory setting and may be both terrestrial and aquatic. Industrial surfaces are particularly prone to the development of biofilms include factory surfaces and the underwater surfaces of boats, drilling rigs etc. As used herein the term "paint" means a solid pigment in a liquid vehicle, used as a decorative or protective coating. In some embodiments, the paint may have the antimicrobial nanoparticles of the invention mixed in. As used herein, the term "dye" means a soluble or insoluble coloring matter either in solution or as a pigment. As used herein the term "pigment" means a powdered substance that is mixed with a liquid in which it is relatively insoluble and used especially to impart color to coating materials (as paints or adhesives or resins) or to inks, plastics, and rubber.

Unless defined otherwise, all technical and scientific terms used herein have the same meanings as commonly understood by one of ordinary skill in the art to which this invention belongs. All publications and patents specifically mentioned herein are incorporated by reference for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

This invention provides antibacterial and antimicrobial surface coatings and dental materials by utilizing the antimicrobial properties of CuQ. An antimicrobial barrier is created by incorporation of CuQ nanoparticles of an appropriate size and at a concentration necessary and sufficient to create a unique bioelectrical environment. The unique bioelectrical environment results in the biocidal effectiveness through a multi-factorial mechanism comprising a combination of the intrinsic leaching of $Cu^{2+}$ CuQ ions and the high surface-to-volume electron sink facilitated by the nanosphere. The result is the constant release of antimicrobial $Cu^{2+}$ into the surrounding environment preventing or inhibiting the growth of bacteria. The presence of ionic CuQ results in inhibiting or delaying bacterial destruction and endogenous enzymatic breakdown of the zone of resin inter-diffusion, the integrity of which is essential for dental restoration longevity.

It has been discovered that other factors, in addition to bacteria, may play a key role in the degradation of the adhesive, and high failure rate of resin composite restorations. In dental restorations, a special resin, the dental adhesive, is engineered to penetrate the tooth surface and bond the filling material to the tooth. It is placed in a thin coat, in a separate step prior to placing the filling material. The filling material is called a "composite resin" and provides the actual restoration. Both materials contain resin and both can be modified with the antimicrobial nanoparticles. Specifically, endogenous dentin proteases are responsible for collagen destruction in the resin interdiffusion zone also called the hybrid layer. Etched dentin is composed of 30 vol. % collagen, and virtually no mineral phase. During bonding, the dissolved mineral phase gets replaced with resin and the newly exposed collagen network is enveloped with adhesive. Once light cured, the adhesive resin forms a micromechanical lock around billions of collagen fibrils, holding the newly formed biosynthetic layer together. Collagen integrity is essential to dentin bond strength and longevity.

For millennia metallic CuQ has been recognized as a potent microbicidal agent. The inventors recognized that the continuously active antimicrobial properties of CuQ and its compounds may effectively retard the invasion and proliferation of inherent microorganisms resident in the oral cavity. The inventors have identified that the incorporation of a sufficient quantity of CuQ into the adhesive layer of the restoration may result in the formation of a continuously active antimicrobial barrier. As disclosed herein, an antimicrobial barrier can be created by incorporation of CuQ nanoparticles of an appropriate size and at a concentration necessary and sufficient to create a unique bioelectrical environment. The unique bioelectrical environment results in the biocidal effectiveness through a multi-factorial mechanism through a combination of the intrinsic leaching of CuQ ions and the high surface-to-volume electron sink facilitated by the nanosphere/nanoparticle. Thus, a combination, previously unrecognized, of a universally distributed electron sink and routine ionic flux of CuQ ions will facilitate an intimate and lethal interaction with the invading microbes.

The inventors' knowledge of current dental bonding techniques has identified numerous deficiencies. For example, bacterial microleakage resulting in recurrent caries is the principle cause of failure most frequently observed when employing Resin Based Composite (RBC) solutions for the restoration of a carious lesion in humans. Bacterial invasion has been found to be 3.5 times higher in RBC restorations than in restorations composed of High Copper Amalgams (HCA). However, it should be noted that copper is used in amalgams due to its physical properties. The increased copper content of HCA is thought to provide greater strength, less tarnish and corrosion, and less creep. However, an antibacterial role for copper in amalgam has not been recognized. The evaluation of 650 radiographs of interproximal restorations found that 43% of the restorations employing RBC failed as a consequence of recurrent decay while only 8% for those using HCA. RBC microleakage with subsequent bacterial invasion occurs at the restoration/tooth interface. This interface is called the adhesive layer, a biosynthetic layer consisting of interlocking Type I collagen and the adhesive resin found in the RBC bonding systems. The adhesive layer is the limiting link implicated in the failure of RBC restorations resulting in recurrent carries.

In addition, nonbacterial destruction of collagen in the hybrid layer may account for premature resin composite failure. Dentin contains matrix metalloproteinases-2, -8 and -9 (MMP's) that slowly degrade the collagen network essential to the micromechanical bond. If the bond is destroyed the restoration will succumb to microleakage, bacterial invasion and failure. CuQ has recently been shown to be a potent MMP inhibitor. CuQ nanoparticles will prevent collagen breakdown in the hybrid layer which is a serious problem facing modern bonding agents. Although it is uncertain how large a role MMP's play in bond degradation, research shows that inhibiting MMP's with 2% chlorhexidine gluconate prior to adhesive application prevents bond degradation and increases longevity. Amalgam has been shown to release CuQ and inhibit the gelatinase MMP-2 and MMP-9, possibly contributing to the clinical success of HCA restorations. This success is of importance because the bond strength longevity of the CuQ nanoparticle adhesive, according to the invention is hypothesized to be more stable due to the potential ability of CuQ nanoparticles to inhibit endogenous collagenolytic enzymes.

The present invention incorporates CuQ nanoparticles into dental adhesives and other dental materials to solve one of the greatest shortcoming of modern restorative materials by preventing or delaying bacterial destruction and endogenous enzymatic breakdown of the zone of resin inter-diffusion, the integrity of which is essential for restoration longevity.

CuQ+DentalBond

Therefore, in various exemplary embodiments, the invention requires the incorporation of a sufficient concentration of antimicrobial CuQ nanoparticles into an appropriate adhesive matrix in order to create a dental adhesive with inherent antimicrobial properties. The invention described as CuQ+DentalBond will facilitate the establishment of a biosynthetic layer between Type I collagen and resident dental surfaces to form an adhesive layer. CuQ nanoparticles are incorporated into the adhesive resin or composite resin of the bonding system and becomes encased once polymerization of the material occurs. This interlocking of the cured material provides a bondable foundation on which to build a composite resin restoration. Microbacterial attack on this adhesive layer begins almost immediately after placement and eventually leads to microleakage within the adhesive layer and eventual replacement of the restoration due to recurrent decay. Increasing the resistance of the adhesive layer to microbacterial decay would greatly enhance the longevity of these restorations. The invention provides multiple exemplary embodiments based on the principal of incorporating a continuously active antimicrobial agent into a dental adhesive.

CuQ+Caries: In a first embodiment the invention is used in a resin which will increase the life-span of resin based composite fillings through the incorporation of a continuously active antimicrobial agent within the adhesive resin or composite resin used to establish an adhesive layer between the resin based composite filling and the tooth. Replacement of failed dental restorations are presently valued at a 5 billion dollar per year in the United States alone. Current resin based fillings only last 5.7-8 years. The incorporation of Cu+DentalBond within the adhesive should at least double the life span of the resins. This newly developed resin will prevent the primary cause of failure, which is bacterial invasion and destruction of the adhesive/tooth interface.

CuQ+Perio-Prevent: In a second exemplary embodiment, the invention is useful in preventing the development of periodontal disease. This will be accomplished by applying CuQ+DentalBond on the tooth surface immediately below the gum line of the tooth. The continuously active antimicrobial barrier established by the adhesive containing CuQ+DentalBond will prevent the localized invasion of the indigenous microorganisms responsible for the development of periodontal disease. Coupled with routine oral hygiene the CuQ+DentalBond will abrade away requiring its reapplication during routine dental applications.

CuQ+Perio-Contro: In a third exemplary embodiment, the invention is useful in controlling periodontal disease. This will be accomplished by applying Cu+DentalBond on the tooth surface immediately below the gum line of the tooth and within a periodontal pocket >5 mm in depth. The continuously active antimicrobial barrier established by the adhesive containing Cu+DentalBond will prevent the localized invasion of the indigenous microorganisms responsible for the development of periodontal disease. Coupled with routine oral hygiene the Cu+DentalBond will abrade away requiring its reapplication during routine dental applications.

CuQ+Seal: In a fourth exemplary embodiment, the invention prevents the development of dental carries in children as a consequence of sealant application. This will be accomplished by incorporating CuQ+DentalBond in the resin-based dental sealant material. The continuously active antimicrobial barrier established by the sealant containing CuQ+DentalBond will prevent the localized invasion of the indigenous microorganisms responsible for the development of caries under and around dental sealants thus extending their effective lifespan.

CuQ+Plant: In a fifth exemplary embodiment, the invention is useful in insuring the successful establishment of invasive dental implants. This will be accomplished by placing CuQ+DentalBond on the adjacent tooth surfaces and those immediately below the gum line of the surrounding teeth in order to prevent the establishment of an unfavorable concentration of microbes, in this critical area, that limit the successful establishment of osseointegrative dental implants. The continuously active antimicrobial barrier established by the adhesive containing CuQ+DentalBond will prevent the localized invasion of the indigenous microorganisms responsible for the development of unfavorable conditions that result in peri-implantitis. Coupled with routine oral hygiene the CuQ+DentalBond will abrade away requiring its reapplication during routine dental applications until such time as the implant is reading to carry a load.

CuQ+StablePlant: In a sixth exemplary embodiment, the invention is useful in insuring the continued success of invasive dental implants. This will be accomplished by placing CuQ+DentalBond on the adjacent tooth surfaces and those immediately under the crown and associated implant gum line of implant as well as those of the surrounding teeth in order to prevent the establishment and/or retard the further development of unfavorable concentrations of microbes that limit the viability of osseointegrative dental implants. The continuously active antimicrobial barrier established by the adhesive containing CuQ+DentalBond will prevent the localized invasion of the indigenous microorganisms responsible for the development of unfavorable conditions that result in peri-implantitis. Coupled with routine oral hygiene the CuQ+DentalBond will abrade away requiring its reapplication during routine dental applications until such time as the implant is reading to carry a load.

CuQ+Ortho: In a seventh exemplary embodiment, the invention is useful in preventing the development of dental carries in children as a consequence of the application of bands and other appliances used for orthodonture treatment. This will be accomplished by placing CuQ+DentalBond on the tooth surface prior to the placement of orthodonture appliances. The continuously active antimicrobial barrier established by the adhesive containing CuQ+DentalBond will prevent the localized invasion of the indigenous microorganisms underneath the foreign bodies which are thought to be responsible for the development of caries.

Cu+Endo: In an eighth exemplary embodiment, the invention is useful in insuring the success of endodontic procedures. Currently composite resin is used to seal root canals during the obturation procedure. The antimicrobial PCCG coated CuQ nanopraticles can be incorporated into resin root canal sealer to insure that the endodontic treatment does not succumb to microbial attack. This is accomplished by placing CuQ+DentalBond within the root canal as a root canal sealer prior to the placement of packing material. The continuously active antimicrobial barrier established by the adhesive containing CuQ+DentalBond will prevent the localized invasion of the indigenous microorganisms which are thought to be responsible for the failure of the endodontic treatment.

CuQ+Device: In a ninth exemplary embodiment, the invention is useful in providing an antimicrobial layer on any indwelling invasive appliance that will be placed into a patient. Those of skill in the art will appreciate that the coating technology according to the invention has many applications including, but not limited to, temporary, short term applications, such as, the coating of temporary urinary catheters, as well as, longer term or permanent applications including devices such as a portacath, an artificial joint or heart valve, for example.

CuQ+Surface: In a tenth exemplary embodiment, the invention provides an indwelling antimicrobial device. In the invention according to this embodiment, a device having a surface is coated with a resin containing CuQ nanoparticles as described above for CuQ+DentalBond and can be implanted anywhere that will be efficacious for the health of the patient. For example, the patient may have chronic infection such as an infection of the urinary tract or chronic bacterial prostatitis. In these cases the device surface is coated with the CuQ+DentalBond resin or other CuQ nanoparticle containing adhesive and is implanted within the urinary tract or the prostate gland at the site of infection and a continuously active antimicrobial barrier is established by the adhesive containing CuQ+ DentalBond treating the chronic infection in a localized manner. Those of skill in the art will appreciate that the coated surface can be any surface that is acceptable to the body. For example, the surface can be in the form of a stent, suture, staple etc. which can be implanted so as to remain in place at the site of infection. In other exemplary embodiments, the CuQ nanoparticles themselves may form the surface such that the nanoparticles are either held in a containment device or uncontained are implanted directly within tissue at the site of infection or specifically targeted to the site, such as by a specific receptor protein attached to its surface.

The invention, according to this exemplary embodiment, will create antimicrobial surfaces for use within the human body, antimicrobial surfaces to protect the human body, and/or antimicrobial surfaces to control the intrinsic microbial burden found in the environment. In some instances, these "biofilms" are responsible for the distribution of infectious agents within food preparation areas, hospitals, medical clinics, hotels, schools and other places where the control of the burden is required in both medical and industrial settings. An important aspect of the invention is the proper concentration of CuQ necessary and sufficient to create continuously active microbicidal/microbiostatic environment in order to control the growth and distribution of microbes.

As previously discussed, past investigators have attempted to add antimicrobial agents to adhesive resins with different mechanisms. A resin adhesive has been introduced into the market that incorporates an anti-bacterial monomer 12-methacryloyloxydodecylpyridinium bromide (MDPB). MDPB has been shown to be a highly effective antimicrobial agent, without negatively affecting the mechanical properties or color of adhesive resins. However, little evidence exists on the longevity of MDPB's antimicrobial activity and it has been suggested that it is short lived possibly due to the decreased antimicrobial activity after light curing. Further, when the experimental CuQ nanoparticle containing adhesive resin of the instant invention was tested against MDPB containing adhesive resins it was found to be significantly more efficacious at killing and preventing growth of caries related bacteria. This data is presented in FIG. 2. One advantage of the antimicrobial activity of PCCG coated CuQ, previously unappreciated by those of skill in the art, is that the antimicrobial effect of CuQ will last indefinitely.

CuQ+Glass Ionomer

In further recognition of the therapeutic and prophylactic potential of CuQ based bacteriostatic/bacteriocidal materials, the inventors have identified other exemplary embodiments of the invention. These embodiments are based on the identification that a Cu+Glass Ionomer can be used as a bacteriostatic/cidal and anti-collagenolytic restorative material use to control the invasion of microorganisms. Therefore, various other exemplary embodiment of invention requires the incorporation of a sufficient concentration of antimicrobial CuQ nanoparticles into an appropriate polyacrylic acid/fluoroaluminosilicate glass matrix in order to create a dental restorative material with inherent antimicrobial properties.

CuQ+Glass Ionomer (GI): In these exemplary embodiments, the invention includes glass ionomer with CuQ nanoparticles and provides a tooth colored restoration that is able to resist bacterial invasion that plagues all dental restorations. Glass ionomer is a restorative material placed in areas of the mouth where complete isolation from moisture cannot be achieved and therefore composite resin restorations are not able to be used. Traditional glass ionomer restorations leach fluoride into the adjacent tooth structure which is thought to provide some antimicrobial effect. However, over the long term, this fluoride effect subsides and makes these restorations susceptible to microleakage and recurrent decay at the tooth/restoration interface. Incorporation of CuQ into this material will provide a long-term antimicrobial effect that will increase the longevity of these restorations. Therefore, various exemplary embodiments of the invention are based on the principal of incorporating a continuously active antimicrobial agent such as CuQ nanoparticles into a dental restorative material such as glass ionomer.

CuQ+GICaries: A first exemplary embodiment of the invention based on CuQ+GI provides a filling material that will increase the life-span of glass ionomer fillings through the incorporation of a continuously active antimicrobial agent within the material. The cost to replace failed dental restorations are presently valued at a $5 billion per year. Current resin based fillings only last 5 years. The incorporation of CuQ+Glass Ionomer within the material will help increase the lifespan of these restorations.

CuQ+GI Liner: A second embodiment of the invention based on CuQ+GI provides a liner placed under composite resin restorations as a dentin replacement material. The antimicrobial nature of the material coupled with fluoride release and moisture tolerance makes this an ideal liner material. This will eliminate the technique sensitivity and unpredictable results that often accompany modern dentin bonding while protecting the dentin from microleakage and recurrent caries. The incorporation of CuQ+Glass Ionomer within the material should help increase the lifespan of any restoration under which it is placed.

CuQ+GICEM: A third embodiment of the invention based on CuQ+GI provides a cement for crown and bridge restorations. The antimicrobial effect of the CuQ and fluoride release from the glass ionomer should significantly limit the incidence of recurrent caries at the margins of fixed prosthetics. The incorporation of CuQ+Glass Ionomer within the material will provide increased lifespan of fixed prosthetics cemented with this material.

There are numerous aspects of this invention that are unique. The CuQ nanoparticles have been coated with PCCG in the form of PAA. The PCCG coating provides at least 3 functions to the CuQ nanoparticles: (1) it allows for solubility in a hydrophilic media (such as 10-Hydroxyethyl methacrylate found in dental adhesive primers); (2) it provides a mechanism to attach the nanoparticles to the organic resin matrix in dental adhesives to form poly(acrylic acid-co-2-hydroxyethyl methacrylate); and (3) it provides a mechanism for particle attachment to other dental materials including resin modified glass ionomers and traditional glass ionomers of which PCCG is already a component. PCCG decreases nanoparticle agglomeration to provide a more uniformly distributed particle in the restorative materials. This increased solubility is important allowing the antimicrobial effect to spread throughout the restoration/tooth interface. In addition, the CuQ particles are carefully engineered to properly fit between the inter-collagen spaces of etched dentin to allow for complete inter-diffusion of the antimicrobial nanoparticles into the zone of demineralization.

Particle size is an important consideration when fabricating an adhesive resin due to the microstructure and morphology of demineralized dentin. The spaces between resin-infiltrated collagen fibrils in hybrid layers are only 10-30 nm wide, FIG. 1. It is the proper interdiffusion and polymerization of resin into these inter-collagen spaces that is primarily responsible for adherence of the restoration to the tooth. It is essential to have sufficiently small CuQ nanoparticles, based on the nano-morphology of demineralized dentin, which can penetrate the full length of the hybrid layer. It is essential that a sufficient concentration of CuQ nano-spheres be present in order to confer a metallic nature to the particle. The mechanism for bonding involves resin flowing into the inter-collagen spaces of dentin and subsequently being polymerized via a light cured reaction. These inter-collagen spaces are around 20 nm in size. In order for adequate diffusion into these spaces, material particle sizes should be less than 20 nm. In this respect, those of skill in the art will appreciate that while the instant inventors have found that nanoparticles in the range of 10-30 nm are optimum in allowing diffusion of the antimicrobial CuQ nanoparticles within the inter-collagen spaces, for other applications, much larger particles may be used. However, those of skill in the art will also appreciate that larger nanoparticles will provide less surface area by which the microenvironment and antimicrobial effects of CuQ is affected.

Also unique to this material, 10-30 nm nanoparticles will be incorporated into the adhesive resin and dental glass ionomer materials. This size particle will provide a homogenous distribution of CuQ nanoparticles throughout the hybrid layer and be essential to nano-CuQ adhesive resin and glass ionomer success. Furthermore, particles this small are potent due to the large surface area to volume ratio allowing relatively small concentrations to achieve a profound antimicrobial effect.

Likewise, unique to this material is its color. To prevent the negative esthetic impact traditionally associated with adding metals to esthetic restorative materials, copper iodide nanoparticles were used. Copper(I) iodide nanoparticles are white in color, and they do not negatively impact the esthetics of modern dental adhesives or restorative materials. Traditional CuQ mixtures yield a black particle that would be detrimental to the esthetics of the restoration. The combination of the size, color and proper coupling of the metal nanoparticles to the resin matrix has not been achieved in the past.

This material represents a significant and novel bioengineering approach to the dental hybrid layer by utilizing knowledge of demineralized dentin ultra-morphology coupled with an understanding of the optical properties and manufacturing of sufficiently small antimicrobial CuQ coupled to the restorative materials through a PCCG coating. This material creates a unique bacterial resistant zone of resin interdiffusion that will greatly increase the longevity of the restorations.

Without being held to any particular theory, it is thought that the effectiveness of the present invention is based on the antimicrobial properties resulting from the predilection of Cu metal for the acquisition of an electron from the bacterium. The positive resonance charge of the metal captures the electron resulting in the concomitant dissipation of its energy to the metal. The net effective is that the microbe or bacterial population is in a net electrical deficit and resulting in the simultaneous generation of free radicals within the cytoplasm of the microbe or bacterium resulting in death.

PCCG coated CuQ nanoparticles can be incorporated into dental materials to create an antimicrobial and anticalgenolytic dental restorative including dental adhesives, composite resin materials including: cement, sealants, flowable composite, compomers, giomers, nanohybrids, microhybrids, nanofill, ceromers, and endodontic sealant material. It can be incorporated into glass ionomer material and resin modified glass ionomer materials to include cements, liners, bases and filling materials. It can be applied to prevent biofilm formation on root surfaces to prevent root caries, periodontal disease, periimplantitis and recurrent caries. In non-dental uses, the PCCG coated CuQ nanoparticles can be incorporated into adhesives, resins or paints for application to surfaces that inherently develop biofilms, such as in industrial settings or applied to medical devices to inhibit microbial or bacterial infection.

The following paragraphs enumerated consecutively from 1-168 provide for various aspects of the present invention. In a first paragraph (1), the invention provides:

1. An antimicrobial dental resin comprising:
   a dental resin; and
   an antimicrobial amount of CuQ nanoparticles diffused therein.
2. The antimicrobial dental adhesive of paragraph 1, wherein the CuQ nanoparticles are coated in polymer containing carboxylic groups (PCCG).
3. The antimicrobial dental adhesive of paragraph 1 wherein the CuQ nanoparticles have a diameter of 5-30 nm.
4. The antimicrobial dental adhesive of paragraph 3, wherein the CuQ nanoparticles have a diameter of 10-20 nm.
5. The antimicrobial dental adhesive of paragraph 4, wherein the CuQ nanoparticles have a diameter of 15-20 nm.
6. The antimicrobial dental adhesive of paragraph 1, wherein the CuQ nanoparticles have a diameter of 20 nm or less.
7. The antimicrobial dental adhesive of paragraph 1, wherein the CuQ nanoparticles are copper coupled to iodide.
8. The antimicrobial dental adhesive of paragraph 2, wherein the polymer containing carboxylic groups (PCCG) is polyacrylic acid (PAA).
9. An antimicrobial dental sealant comprising:
   a dental sealant; and
   an antimicrobial dental resin including an antimicrobial amount of CuQ nanoparticles diffused therein.
10. The antimicrobial dental sealant of paragraph 9, wherein the CuQ nanoparticles are coated with polymer containing carboxylic groups (PCCG).
11. The antimicrobial dental sealant of paragraph 9, wherein the CuQ nanoparticles have a diameter of 5-30 nm.
12. The antimicrobial dental sealant of paragraph 11, wherein the CuQ nanoparticles have a diameter of 10-20 nm.
13. The antimicrobial dental sealant of paragraph 12, wherein the CuQ nanoparticles have a diameter of 15-20 nm.
14. The antimicrobial dental sealant of paragraph 9, wherein the CuQ nanoparticles have a diameter of 20 nm or less.
15. The antimicrobial dental sealant of paragraph 9, wherein the CuQ nanoparticles are copper coupled to iodide.
16. The antimicrobial dental sealant of paragraph 10, wherein the polymer containing carboxylic groups (PCCG) is polyacrylic acid (PAA).
17. A composition useful in preventing or inhibiting the growth of biofilms on a surface the composition comprising:
   an adhesive containing an antimicrobial amount of CuQ nanoparticles diffused therein; and
   optionally, a paint, dye or pigment.
18. The composition of paragraph 17, wherein the CuQ nanoparticles are coated with PCCG.
19. The composition of paragraph 17, wherein the CuQ nanoparticles have a diameter of 5-200 nm.
20. The composition of paragraph 19, wherein the CuQ nanoparticles have a diameter of 10-100 nm.
21. The composition of paragraph 20, wherein the CuQ nanoparticles have a diameter of 15-50 nm.
22. The composition of paragraph 19, wherein the CuQ nanoparticles have a diameter of 20 nm or less.
23. The composition of paragraph 19, wherein the CuQ nanoparticles are copper coupled to iodide.
24. The composition of paragraph 18, wherein the polymer containing carboxylic groups (PCCG) is polyacrylic acid (PAA).
25. An indwelling antibacterial device implanted in a patient in need thereof at a localized site of infection comprising:
   an implantable surface coated with a an adhesive containing an antimicrobial amount of CuQ nanoparticles diffused therein.
26. The indwelling antibacterial device of paragraph 23, wherein the surface is the surface of a suture, a stent, a staple, a plate, a screw, a pin, a bridge a catheter or a prophylactic device.
27. The device of paragraph 23, wherein the surface is the surface of the nanoparticles, the nanoparticles implanted uncontained or contained within a freely diffusable container.
28. The antimicrobial device of paragraph 23, wherein the CuQ nanoparticles are coated with polymer containing carboxylic groups (PCCG).
29. The antimicrobial device of paragraph 23, wherein the CuQ nanoparticles have a diameter of 5-200 nm.
30. The antimicrobial device of paragraph 29, wherein the CuQ nanoparticles have a diameter of 10-100 nm.
32. The antimicrobial device of paragraph 30, wherein the CuQ nanoparticles have a diameter of 15-50 nm.
33. The antimicrobial device of paragraph 25, wherein the CuQ nanoparticles have a diameter of 20 nm or less.
34. The antimicrobial device of paragraph 25, wherein the CuQ nanoparticles are copper coupled to iodide.
35. The antimicrobial device of paragraph 28, wherein the polymer containing carboxylic groups (PCCG) is polyacrylic acid (PAA)
36. An antibacterial dental restorative composition comprising:
   a glass ionomer or resin modified glass ionomer; and
   an antimicrobial amount of CuQ nanoparticles diffused therein.
37. The antimicrobial dental sealant of paragraph 36, wherein the CuQ nanoparticles are coated in polymer containing carboxylic groups (PCCG).
38. The antimicrobial dental sealant of paragraph 37, wherein the CuQ nanoparticles have a diameter of 5-30 nm.
39. The antimicrobial dental sealant of paragraph 38, wherein the CuQ nanoparticles have a diameter of 10-20 nm.

40. The antimicrobial dental sealant of paragraph 39, wherein the CuQ nanoparticles have a diameter of 15-20 nm.

41. The antimicrobial dental sealant of paragraph 36, wherein the CuQ nanoparticles have a diameter of 20 nm or less.

42. The antimicrobial dental sealant of paragraph 36, wherein the CuQ nanoparticles are copper coupled to iodide.

43. The antimicrobial dental sealant paragraph 37, wherein the polymer containing carboxylic groups (PCCG) is polyacrylic acid (PAA).

44. An antimicrobial sealant for use in dental restorations comprising:
    a glass ionomer or resin modified glass ionomer; and
    an antimicrobial amount of CuQ nanoparticles diffused in the glass ionomer or resin modified glass ionomer.

45. The antimicrobial dental sealant of paragraph 44, wherein the CuQ nanoparticles are coated with polymer containing carboxylic groups (PCCG).

46. The antimicrobial dental sealant of paragraph 44, wherein the CuQ nanoparticles have a diameter of 5-30 nm.

47. The antimicrobial dental sealant of paragraph 46, wherein the CuQ nanoparticles have a diameter of 10-20 nm.

48. The antimicrobial dental sealant of paragraph 47, wherein the CuQ nanoparticles have a diameter of 15-20 nm.

49. The antimicrobial dental sealant of paragraph 44, wherein the CuQ nanoparticles have a diameter of 20 nm or less.

50. The antimicrobial dental sealant of paragraph 44, wherein the CuQ nanoparticles are copper coupled to iodide.

51. The antimicrobial sealant of paragraph 44, wherein the sealant is a phosphate (zinc phosphate, silico phosphate) cement, a polycarboxylate (zinc polycarboxylate, glass ionomer) cement, a phenolate (zinc oxide-eugenol and EBA) cement and a resin (polymeric) cement.

52. The antimicrobial sealant of paragraph 45, wherein the polymer containing carboxylic groups (PCCG) is polyacrylic acid (PAA).

53. A method of preventing tooth decay comprising: applying a CuQ nanoparticle containing dental resin to a tooth surface.

54. The method of paragraph 53, wherein the CuQ nanoparticle containing resin is applied above the gum line.

55. The method of paragraph 53, where the CuQ nanoparticle containing resin is applied below the gum line.

56. The method of paragraph 53, wherein the CuQ nanoparticles have a diameter of 5-30 nm.

57. The method of paragraph 56, wherein the CuQ nanoparticles have a diameter of 10-20 nm.

58. The method of paragraph 57, wherein the CuQ nanoparticles have a diameter of 15-20 nm.

59. The method of paragraph 53, wherein the CuQ nanoparticles have a diameter of 20 nm or less.

60. The method of paragraph 53, wherein the CuQ nanoparticles are coated with polymer containing carboxylic groups (PCCG).

61. The method of paragraph 60, wherein the polymer containing carboxylic groups (PCCG) is polyacrylic acid (PAA).

62. The method of paragraph 53, wherein the CuQ nanoparticles are copper coupled to iodide.

63. A method to prevent or inhibit periodontal disease comprising:
applying a CuQ nanoparticle containing dental resin within a periodontal pocket.

64. The method of paragraph 55 where the CuQ nanoparticle containing resin is applied below the gum line.

65. The method of paragraph 55, wherein the CuQ nanoparticles have a diameter of 5-30 nm.

66. The method of paragraph 57, wherein the CuQ nanoparticles have a diameter of 10-20 nm.

67. The method of paragraph 58, wherein the CuQ nanoparticles have a diameter of 15-20 nm.

68. The method of paragraph 55, wherein the CuQ nanoparticles have a diameter of 20 nm or less.

69. The method of paragraph 55, wherein the periodontal pocket is greater than 5 mm in depth.

70. The method of paragraph 55, wherein the CuQ nanoparticles are coated with PCCG.

71. The method of paragraph 55, wherein the CuQ nanoparticles are copper coupled to iodide.

72. The method of paragraph 70, wherein the polymer containing carboxylic groups (PCCG) is polyacrylic acid (PAA).

73. A method of preventing dental or inhibiting caries comprising:
    applying an antimicrobial dental sealant to a tooth the antimicrobial sealant including an antimicrobial dental resin including an antimicrobial amount of CuQ nanoparticles diffused therein.

74. The method of paragraph 73, wherein the tooth is a child's tooth.

75. The method of paragraph 73, wherein the CuQ nanoparticles have a diameter of 5-30 nm.

76. The method of paragraph 75, wherein the CuQ nanoparticles have a diameter of 10-20 nm.

77. The method of paragraph 76, wherein the CuQ nanoparticles have a diameter of 15-20 nm.

78. The method of paragraph 63, wherein the CuQ nanoparticles have a diameter of 20 nm or less.

79. The method of paragraph 73, wherein the CuQ nanoparticles are coated with PCCG.

80. The method of paragraph 79, wherein the polymer containing carboxylic groups (PCCG) is polyacrylic acid (PAA).

81. The method of paragraph 73, wherein the CuQ nanoparticles are copper coupled to iodide.

82. A method for increasing the successful establishment of dental implants comprising:
    applying an antimicrobial dental resin to a critical area including the adjacent tooth surfaces and those immediately below the gum line of the teeth surrounding the implant, the antimicrobial dental resin including an antimicrobial amount of CuQ nanoparticles diffused therein.

83. The method of paragraph 82, wherein the CuQ nanoparticles have a diameter of 5-30 nm.

84. The method of paragraph 83, wherein the CuQ nanoparticles have a diameter of 10-20 nm.

85. The method of paragraph 84, wherein the CuQ nanoparticles have a diameter of 15-20 nm.

86. The method of paragraph 82, wherein the CuQ nanoparticles have a diameter of 20 nm or less.

87. The method of paragraph 82, wherein the CuQ nanoparticles are coated with polymer containing carboxylic groups (PCCG).

88. The method of paragraph 82, wherein the antimicrobial dental resin is applied to the critical area prior to implantation of the implant.

89. The method of paragraph 82, wherein the antimicrobial dental resin is applied to the critical area one or more times after implantation of the implant.

90. The method of paragraph 82, wherein the implant is an osseointegrative implant.

91. The method of paragraph 82, wherein the CuQ nanoparticles are copper coupled to iodide.

92. The method of paragraph 87, wherein the polymer containing carboxylic groups (PCCG) is polyacrylic acid (PAA).

93. A method for inhibiting the localized invasion of microorganisms in a critical area of a dental implant comprising:
applying an antimicrobial dental resin to the critical area of the site of the implant wherein the antimicrobial dental resin includes an antimicrobial amount of CuQ nanoparticles diffused therein.

94. The method of paragraph 93, wherein the critical area is the adjacent tooth surfaces and those immediately under the crown and associated implant gum line of implant as well as those of the surrounding teeth.

95. The method of paragraph 93, wherein the CuQ nanoparticles have a diameter of 5-30 nm.

96. The method of paragraph 95, wherein the CuQ nanoparticles have a diameter of 10-20 nm.

97. The method of paragraph 96, wherein the CuQ nanoparticles have a diameter of 15-20 nm.

98. The method of paragraph 93, wherein the CuQ nanoparticles have a diameter of 20 nm or less.

99. The method of paragraph 93, wherein the CuQ nanoparticles are coated with polymer containing carboxylic groups (PCCG).

100. The method of paragraph 93, wherein the antimicrobial dental resin is applied prior to implantation of the implant.

101. The method of paragraph 93, wherein the antimicrobial dental resin is applied to the critical area one or more times after implantation of the implant.

102. The method of paragraph 93, wherein the implant is an osseointegrative implant.

103. The method of paragraph 93, wherein the CuQ nanoparticles are copper coupled to iodide.

104. The method of paragraph 99, wherein the polymer containing carboxylic groups (PCCG) is polyacrylic acid (PAA).

105. A method of reducing the incidence of dental carries resulting from the placement of orthodontic appliances in a patient comprising:
applying an antimicrobial dental resin to the surface of a tooth at the site of attachment of orthodontic bands, wherein the antimicrobial dental resin includes an antimicrobial amount of CuQ nanoparticles diffused therein.

106. The method of paragraph 105, wherein the CuQ nanoparticles have a diameter of 5-30 nm.

107. The method of paragraph 106, wherein the CuQ nanoparticles have a diameter of 10-20 nm.

108. The method of paragraph 105, wherein the CuQ nanoparticles have a diameter of 15-20 nm.

109. The method of paragraph 105, wherein the CuQ nanoparticles have a diameter of 20 nm or less.

110. The method of paragraph 105, wherein the CuQ nanoparticles are coated with polymer containing carboxylic groups (PCCG).

111. The method of paragraph 105, wherein the antimicrobial dental resin is applied prior to placement of the orthodontic appliance.

112. The method of paragraph 105, wherein the antimicrobial dental resin is applied to the tooth one or more times after placement of the orthodontic appliance.

113. The method of paragraph 105, wherein the CuQ nanoparticles are copper coupled to iodide.

114. The method of paragraph 110, wherein the polymer containing carboxylic groups (PCCG) is polyacrylic acid (PAA).

115. A method for increasing the success of endodontic procedures comprising:
treating the site of the endodontic procedure with an antimicrobial dental resin to the prior to packing the site with packing materials, wherein the antimicrobial dental resin includes an antimicrobial amount of CuQ nanoparticles diffused therein.

116. The method of paragraph 115, wherein the endodontic procedure is a root canal, endodontic retreatment, surgery, cracked teeth, and dental trauma.

117. The method of paragraph 115, wherein the CuQ nanoparticles have a diameter of 5-30 nm.

118. The method of paragraph 117, wherein the CuQ nanoparticles have a diameter of 10-20 nm.

119. The method of paragraph 118, wherein the CuQ nanoparticles have a diameter of 15-20 nm.

120. The method of paragraph 115, wherein the CuQ nanoparticles have a diameter of 20 nm or less.

121. The method of paragraph 115, wherein the CuQ nanoparticles are coated with polymer containing carboxylic groups (PCCG).

122. The method of paragraph 121, wherein the polymer containing carboxylic groups (PCCG) is polyacrylic acid (PAA).

123. The method of paragraph 115, wherein the CuQ nanoparticles are copper coupled to iodide.

124. A method of inhibiting or limiting the infection resulting from the insertion of an indwelling invasive appliance in a patient comprising:
coating the surface of the indwelling invasive appliance with an antimicrobial composite resin or adhesive resin prior inserting the indwelling appliance in the patient, wherein the antimicrobial resin/adhesive includes an antimicrobial amount of CuQ nanoparticles diffused therein.

125. The method of paragraph 124, wherein the indwelling invasive appliance is a short-term device or a long-term device.

126. The method of paragraph 125, wherein the indwelling device is a urinary catheter, a portacath, a stent, a pacemakers, a heart valve, bypass grafts, artificial joints, and central nervous system shunts.

127. The method of paragraph 124, wherein the CuQ nanoparticles have a diameter of 5-30 nm.

128. The method of paragraph 127, wherein the CuQ nanoparticles have a diameter of 10-20 nm.

129. The method of paragraph 128, wherein the CuQ nanoparticles have a diameter of 15-20 nm.

130. The method of paragraph 124, wherein the CuQ nanoparticles have a diameter of 20 nm or less.

131. The method of paragraph 124, wherein the CuQ nanoparticles are coated with polymer containing carboxylic groups (PCCG).

132. The method of paragraph 131, wherein the polymer containing carboxylic groups (PCCG) is polyacrylic acid (PAA).

133. A method of inhibiting or reducing the establishment of biofilms on a surface comprising:
coating the surface with an antimicrobial adhesive, adhesive resin or composite resin, wherein the antimicrobial adhesive, adhesive resin or composite resin includes an antimicrobial amount of CuQ nanoparticles diffused therein.

134. The method of paragraph 133, wherein the surface is the surface of a medical device or an industrial device.

135. The method of paragraph 133, wherein the CuQ nanoparticles have a diameter of 5-200 nm.

136. The method of paragraph 135, wherein the CuQ nanoparticles have a diameter of 10-100 nm.

137. The method of paragraph 136, wherein the CuQ nanoparticles have a diameter of 15-50 nm.

138. The method of paragraph 133, wherein the CuQ nanoparticles have a diameter of 20 nm or less.

139. The method of paragraph 133, wherein the CuQ nanoparticles are coated with polymer containing carboxylic groups (PCCG).

140. The method of paragraph 139, wherein the polymer containing carboxylic groups (PCCG) is polyacrylic acid (PAA).

141. The method of paragraph 133, wherein the adhesive contains a paint, a dye or pigment.

142. The method of paragraph 121, wherein the CuQ nanoparticles are copper coupled to iodide.

143. A method of treating an internal infection comprising: implanting a surface coated with an adhesive, composite adhesive or resin containing an antimicrobial amount of CuQ nanoparticles diffused therein.

144. The method of paragraph 143, wherein the surface is the surface of a suture, a stent, a staple, a plate, a screw, a pin, a bridge, a catheter or a prophylactic device.

145. The method of paragraph 143, wherein the surface is the surface of the CuQ nanoparticles either uncontained or contained within a freely diffusable container.

146. The method of paragraph 143, wherein the CuQ nanoparticles are coated with polymer containing carboxylic groups (PCCG).

147. The method of paragraph 143, wherein the CuQ nanoparticles have a diameter of 5-200 nm.

148. The method of paragraph 147, wherein the CuQ nanoparticles have a diameter of 10-100 nm.

149. The method of paragraph 148, wherein the CuQ nanoparticles have a diameter of 15-50 nm.

150. The method of paragraph 143, wherein the CuQ nanoparticles have a diameter of 20 nm or less.

151. The method of paragraph 143, wherein the CuQ nanoparticles are copper coupled to iodide.

152. The method of paragraph 146, wherein the polymer containing carboxylic groups (PCCG) is polyacrylic acid (PAA).

153. A method of inhibiting or preventing the development of dental caries in a patient the method comprising:
coating surface of a tooth with a restorative material including a glass ionomer containing an antimicrobial amount of CuQ nanoparticles diffused therein.

154. The method of paragraph 153, wherein the CuQ nanoparticles have a diameter of 5-30 nm.

155. The method of paragraph 154, wherein the CuQ nanoparticles have a diameter of 10-20 nm.

156. The method of paragraph 155, wherein the CuQ nanoparticles have a diameter of 15-20 nm.

157. The method of paragraph 153, wherein the CuQ nanoparticles have a diameter of 20 nm or less.

158. The method of paragraph 153, wherein the CuQ nanoparticles are coated with polymer containing carboxylic groups (PCCG).

159. The method of paragraph 158, wherein the polymer containing carboxylic groups (PCCG) is polyacrylic acid (PAA).

160. The method of paragraph 153, wherein the CuQ nanoparticles are copper coupled to iodide.

161. A method for increasing the bonding and life span of dental restorations comprising:
placing a liner material under a composite resin restoration, the liner material comprising a glass ionomer containing an antimicrobial amount of CuQ nanoparticles diffused therein.

162. The method of paragraph 161, wherein the CuQ nanoparticles have a diameter of 5-30 nm.

163. The method of paragraph 162, wherein the CuQ nanoparticles have a diameter of 10-20 nm.

164. The method of paragraph 163, wherein the CuQ nanoparticles have a diameter of 15-20 nm.

165. The method of paragraph 161, wherein the CuQ nanoparticles have a diameter of 20 nm or less.

166. The method of paragraph 161, wherein the CuQ nanoparticles are coated with polymer containing carboxylic groups (PCCG).

167. The method of paragraph 166, wherein the polymer containing carboxylic groups (PCCG) is polyacrylic acid (PAA).

168. The method of paragraph 161, wherein the CuQ nanoparticles are copper coupled to iodide.

Various exemplary embodiments of devices and compounds as generally described above and methods according to this invention will be understood more readily by reference to the following examples, which are provided by way of illustration and are not intended to be limiting of the invention in any fashion.

Example 1

Dental Materials Containing CuQ Iodide Nanoparticles

Figure 2:
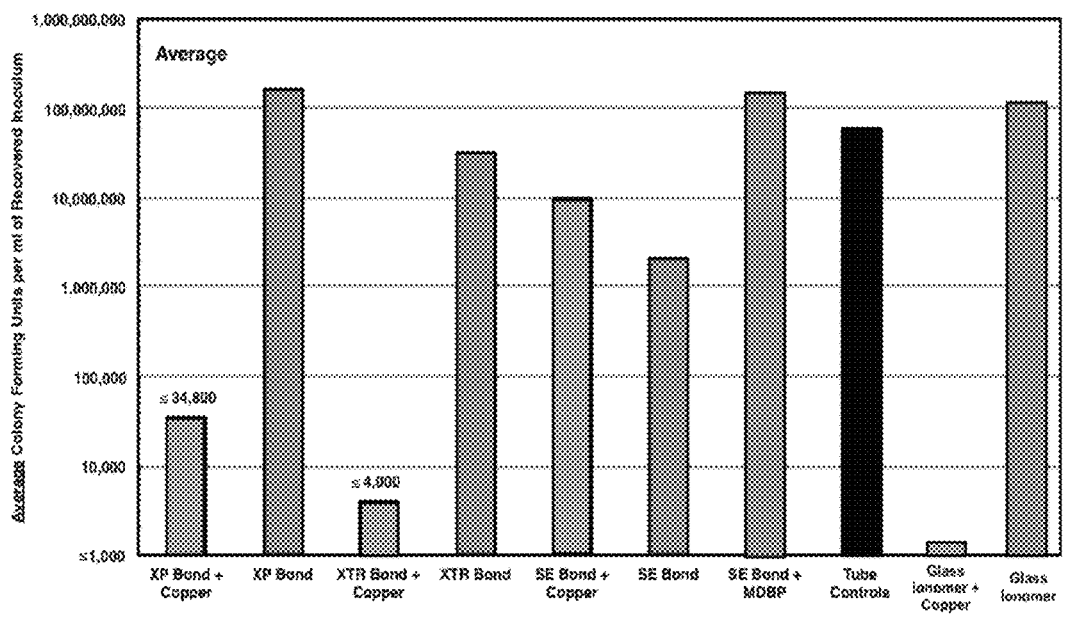
FIG. 2 is a graph illustrating the antimicrobial properties of polyacrylic acid (PAA) coated CuQ iodide nanoparticle-modified adhesive resin compared to the control and commercially available resins.
Figure 3:
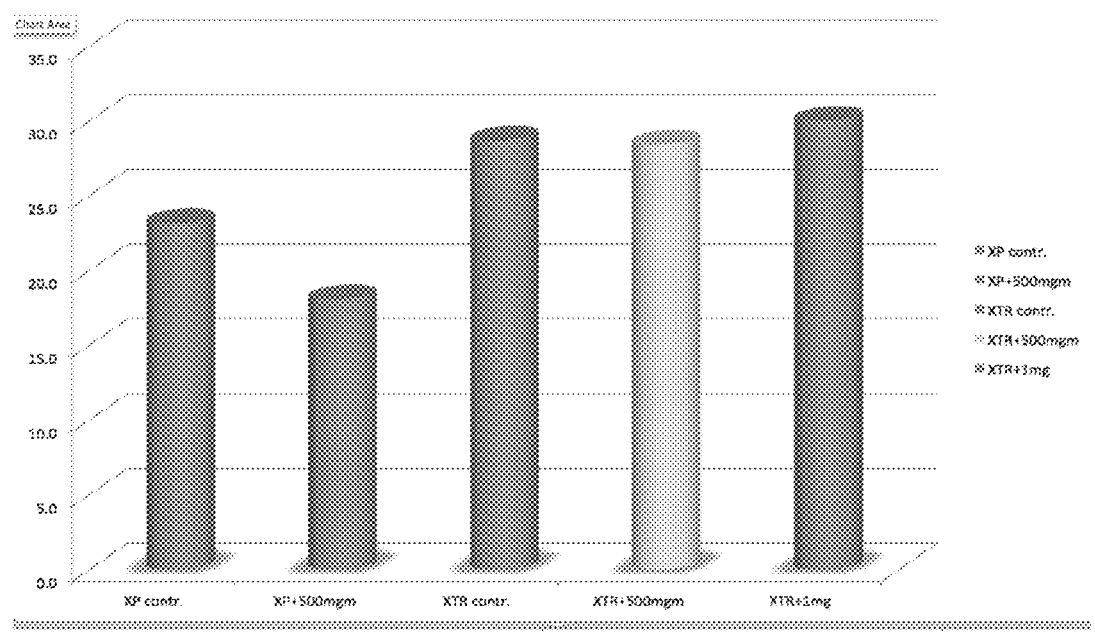
FIG. 3 is a graph illustrating the bond strength of CuQ-modified adhesive and unaltered adhesives.

The inventors have successfully produced dental materials containing copper iodide nanoparticles and have shown the material to maintain the esthetics, rheology and adhesive capabilities of the unaltered materials while providing an antimicrobial affect. Furthermore, the adhesive resin and glass ionomer with copper iodide nanoparticles was 7 orders of magnitude more antimicrobial than the current material marketed as being antimicrobial. These results are shown in FIG. 2. As shown, when the experimental CuQ nanoparticle containing adhesive resin was tested against MDPB containing adhesive resins it was found to be significantly more efficacious at killing and preventing growth of caries related bacteria. In addition, FIG. 3 shows the bond strength of the copper modified adhesive materials is unaltered from that of the controls.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative not limiting. Various changes may be made without departing from the spirit and scope of the invention. Therefore, the invention is intended to embrace all known or later-developed alternatives, modifications, variations, improvements and/or substantial equivalents of these exemplary embodiments.

Example 2

Synthesis of PAA Coated CuQ Oxide Nanoparticles

Copper Oxide Nanoparticle Synthesis: A stock solution of 120 ppm copper solution is made by first dissolving 12 mg Cu₂O completely in 10 mL NH₄OH before diluting with 90 mL of ultrapure 18 MΩ H₂O. In a 20 mL scintillation vial, 10 mL of the 120 ppm copper stock solution and 50 µL of a 1% (w/w) PAA were added. In a separate 1 dr vial, 2 mg NaBH₄ was dissolved in 2.5 mL H₂O and sonicated briefly to mix before injecting 2 mL of the NaBH₄ solution directly into the copper solution. The vial was capped and swirled until it turned a uniform light yellow or yellow-brown. It was allowed to age for 1 hour until it turns a deep red color. The solution was then bubbled with N₂ gas until all of the NH₄OH has been removed. The vial was capped quickly to prevent the least amount of air from entering the vial.

Example 3

Synthesis of PAA Coated CuQ Iodide Nanoparticles

Copper Iodide Particle Synthesis: In an Erlenmeyer flask, 78.8 mL of 0.2M copper (copper (II) sulfate) and 7.8 mL of 20% (w/w) PAA was mixed. Then 100 mL of 0.4M iodide (potassium iodide) was added to the flask and thoroughly mixed producing a white powder. An additional 50 mL of 0.4M iodide solution was added to complete the reaction. The powder was washed with water by centrifugation four times before drying in a vacuum oven at 50° C.

Example 4

Synthesis of PAA Coated CuQ Sulfide Nanoparticles

Copper Sulfide Particle Synthesis: In an Erlenmeyer flask, 78.8 mL of 0.2M copper (copper (II) sulfate) and 7.8 mL of 20% (w/w) PAA was mixed. Then 100 mL of 0.2M sulfide (sodium sulfide) was added to the flask and thoroughly mixed producing a dark powder. An additional 50 mL of 0.2M sulfide solution was added to complete the reaction. The dark bluish-black powder was washed with water by centrifugation four times before drying in a vacuum oven at 60° C.

Example 5

Mixing of PAA Coated CuQ Nanoparticles into Dental Resin

The PAA coated nanoparticles were mixed into the dental resin using a sonicator under dark conditions in an iced-water bath for 60 seconds. The dental resin (Optibond™ XTR (Kerr) and XP Bond® (Dentsply)) was mixed at a ratio of 500 micrograms (Copper nanoparticle)/1 ml of resin and 1000 micrograms/ml. Both concentrations were effective. The glass ionomers used were Vitrebond™ (3M) and Ionofil® (Voco).

Example 6

Bacterial Growth in Copper Nanoparticle Containing Dental Adhesive

The bacterial type strain used was: *Streptococcus mutans*, ATCC® 25175™.
Cultures were grown at 37° C. under anaerobic conditions using the BD GasPak™ EZ Anaerobe Container System (BD 260678) in BBL™ Brain Heart Infusion broth (BD 211059) (BHIB) and/or BBL™ Brain Heart Infusion Agar (BD 221570) (BHIA).
Disk Preparation: The commercial control adhesives (Optibond™ XTR, Kerr, and XP Bond®, Dentsply) as well as the copper nanoparticle impregnated adhesive were placed on one side of a prefabricated composite material disc (Clearfil AP-X, Kuraray, Osaka, Japan) of 10 mm in diameter. The surface will be covered with a celluloid strip (GC, Tokyo, Japan) and light cured for 40 s with a light activation unit (Valo®, Ultradent). The disks were randomly divided to receive a coat of either commercial resin or experimental resin. After a uniform adhesive resin was applied it was light cured for 40 seconds (Valo®, Ultradent). The disks to be analyzed were placed in individual 18×150 mm test tubes and immersed in 10 ml of sterile, deionized, distilled water and agitated at 200 rpm at 37° C. for two hours. Each disk was transferred to individual 35×10 mm Fisherbrand disposable petri dish (Cat. No. 0875711YZ) and air-dried for at least twenty-four hours. The disks were then ethanol sterilized for 10 minutes by adding 5-7 ml of 70% ETOH (prepared with Pharmco-Aaper 200 proof, Absolute, Anhydrous ACS/USP grade ETOH (Cat. No. 111000200) to each dish. The disks were air dried for at least 48 hours.

Inoculum: Overnight cultures of *Streptococcus mutans*, ATCC® 25175™ were vigorously vortexed and, using an Eppendorf BioPhotometer, the $OD_{600}$ was adjusted to between $0.72_A$-$0.74_A$. The inoculum concentration for each set of disks was determined by making dilutions of the adjusted suspension in BHIB through $10^{-8}$ and plating the dilutions on BHIA. The plates were incubated anaerobically for 48 hours. The colony counts ranged from $7.3 \times 10^{-7}$ to $7.9 \times 10^{-9}$ cells/ml.

Figure 4:
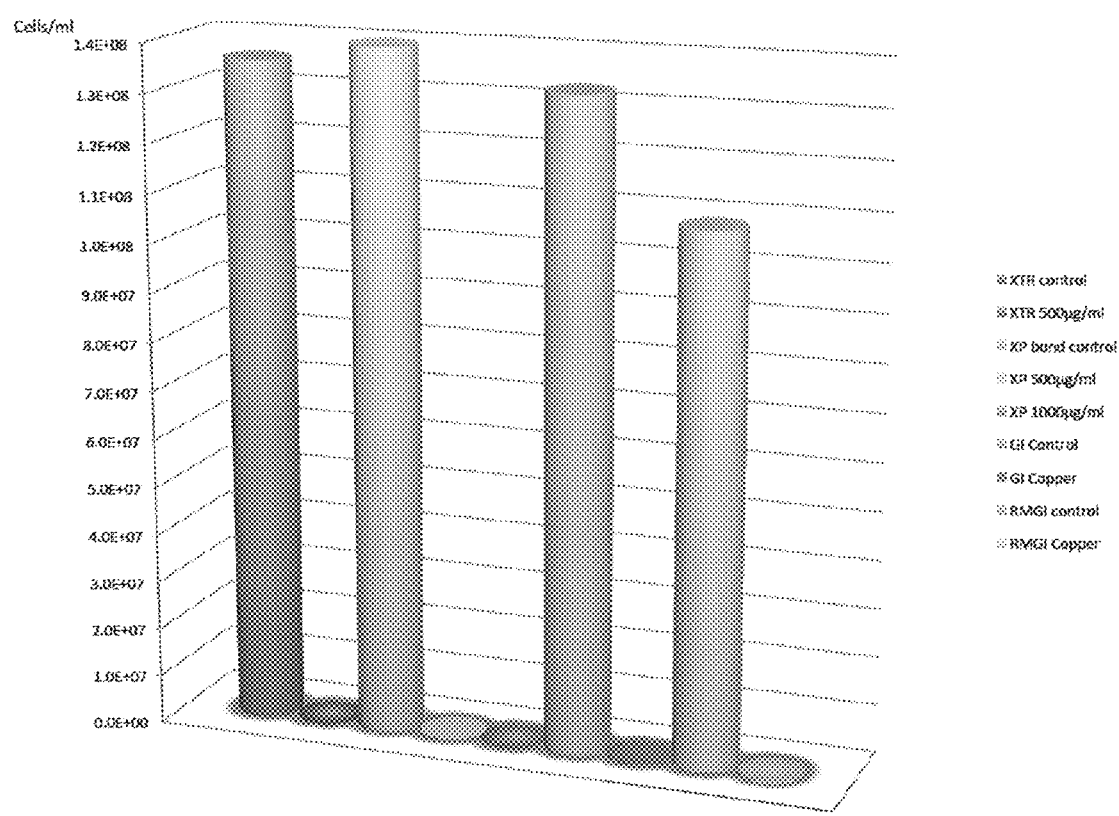
FIG. 4 is a graph illustrating the total recovered bacteria/ml from the experimental copper nanoparticle dental materials is compared to the standard commercially available materials.

100 µl of the adjusted bacterial suspension was spread over each disk surface. Also, 100 µl of the adjusted bacterial suspension was placed into three 1.5 ml snap cap tubes to be run as controls. The inoculated disks and tubes were incubated anaerobically at 37° C. for 18 hours. Using aseptic technique the disks were transferred to a tube containing 9.9 ml of sterile BHIB. The 100 µl of culture from the snap cap tubes was transferred into 9.9 ml of BHIB, the tubes rinsed with broth from these dilution tubes and the rinse returned to the same tube. All tubes were then vortexed for 3 minutes. Dilutions were made in BHIB through $10^{-6}$ and plated on BHIA. The plates were incubated anaerobically at 37° C. for 48 hours then the colonies were counted and reported as cells/ml. These data are presented in FIG. 4, illustrating that in all cases the copper nanoparticle containing adhesive had significantly fewer colony forming units than the non-copper nanoparticle containing controls, $p<0.05$.

While this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:
1. An antimicrobial dental device, material, or implant comprising an antimicrobial amount of copper iodide (CuI) nanoparticles diffused therein or disposed thereon, wherein the dental device is a dental crown and the dental material is selected from the group consisting of a dental sealant, and a dental resin.

2. The antimicrobial dental device, material, or implant of claim 1, wherein the copper iodide nanoparticles are coated with a polymer containing carboxylic groups (PCCG).

3. The antimicrobial dental device, material, or implant of claim 2, wherein the PCCG is a polyacrylic acid polymer (PAA).

4. The antimicrobial dental device, material, or implant of claim 1, wherein the copper iodide nanoparticles have a diameter of 5-30 nm.

5. The antimicrobial dental device, material, or implant of claim 1, wherein the dental material is a dental sealant.

6. The antimicrobial dental device, material, or implant of claim 5, wherein the dental sealant is a phosphate cement, a polycarboxylate cement, a phenolate cement or a polymeric cement.

7. The antimicrobial dental device, material, or implant of claim 1, wherein the dental material is a glass ionomer.

8. The antimicrobial dental device, material, or implant of claim 7, wherein the glass ionomer is a resin modified glass ionomer.

9. An antimicrobial implant as recited by claim 1.

10. An antimicrobial crown as recited by claim 1.

11. The antimicrobial dental device, material, or implant of claim 6, wherein the dental sealant is zinc phosphate, silico phosphate, zinc polycarboxylate, glass ionomer, zinc oxide-eugenol and EBA (ethoxybenzoic acid) or a polymeric resin cement.

12. A method of treating or preventing tooth decay or periodontal disease comprising applying an antimicrobial dental material in accordance with claim 1 to a tooth surface.

13. The method of claim 12, wherein the antimicrobial material is applied above the gum line.

14. A method for increasing the successful establishment of a dental implant comprising applying an antimicrobial dental material in accordance with claim 1 to an area including the adjacent tooth surfaces and those immediately below the gum line of the teeth surrounding the implant.

15. The method of claim 14, wherein the implant is an osseointegrative implant.

16. A method for carrying out an endodontic procedure comprising treating the site of the procedure with an antimicrobial dental material in accordance with claim 1.

17. The method of claim 16, wherein the site of the endodontic procedure is treated with the antimicrobial dental material prior to packing said site with packing materials.

18. The method of claim 17, wherein the endodontic procedure is a root canal, endodontic retreatment, surgery, treating cracked teeth, and treating dental trauma.

* * * * *